United States Patent [19]

McParland

[11] 4,307,719
[45] Dec. 29, 1981

[54] HYPERALIMENTATION CATHETER AND METHOD OF USE

[76] Inventor: Felix A. McParland, 4841 E. Lake Harriet Blvd., Minneapolis, Minn. 55409

[21] Appl. No.: 96,998

[22] Filed: Nov. 23, 1979

[51] Int. Cl.³ .................... A61M 5/00; A61M 27/00
[52] U.S. Cl. ........................ 128/214 R; 128/350 R
[58] Field of Search ............... 128/214 R, 349, 350, 128/214

[56] References Cited

U.S. PATENT DOCUMENTS

| | | | |
|---|---|---|---|
| 3,176,690 | 4/1965 | H'Doubler | 128/348 |
| 3,461,869 | 8/1969 | Hargest | 128/214 |
| 3,654,932 | 4/1972 | Newkirk | 128/350 V |
| 3,663,965 | 5/1972 | Lee, Jr. et al. | 128/214 R |
| 3,777,761 | 12/1973 | Sheridan | 128/350 R |
| 3,821,957 | 7/1974 | Riely et al. | 128/348 R |

OTHER PUBLICATIONS

Merrill et al., The Use of the Inlying Plastic Conduit for Chronic Peritoneal Irrigation, 8 *Transactions of the American Society for Artificial Organs*, pp. 252–255 (1962).

Telander, M.D. et al., *Hypertonic Parenteral Alimentation*, Minnesota Medicine, vol. 54, pp. 985–988 (1971).

*Primary Examiner*—Stephen C. Pellegrino
*Attorney, Agent, or Firm*—Merchant, Gould, Smith, Edell, Welter & Schmidt

[57] ABSTRACT

Catheters (1) are constructed from a catheter tube (2) to which is firmly attached a transverse cross bar or wing (3). The improved catheter is particularly well suited for hyperalimentation of infants. In use, an incision is made in the patient, usually behind the right ear, and the tail of the catheter is routed through the incision under the skin to a remote exit point which is usually on the neck. The catheter tube (2) is then withdrawn from the exit point until the wing (3) is pulled into the incision. The incision is then closed so as to firmly lock the wing and catheter in place. The tail of the catheter is then cut to the desired length and the tail is introduced into an appropriate vein (e.g. the external jugular vein). The opposite or inlet end of the catheter tube is then connected to a suitable source of infusate and alimentation is begun.

2 Claims, 4 Drawing Figures

HYPERALIMENTATION CATHETER AND METHOD OF USE

TECHNICAL FIELD

This invention relates to catheters primarily intended for the intravenous alimentation of infants and children. The catheter is characterized by a small transverse wing or cross member which is firmly attached to the catheter tubing.

BACKGROUND OF PRIOR ART

Infant mortality in a host of newborn gastrointestinal disturbances is often primarily related to the effects of starvation. For many years, investigators sought to develop an artificial method for delivering the nutrients necessary for heatling with normal growth and development, but such attempts generally failed. However, in 1967 several investigators reported a new technique which allowed prolonged hypertonic intravenous alimentation with resultant normal growth and development in puppies. Since then, this method has been utilized successfully in adults, children, and infants. This technique involves inserting a catheter into an appropriate vein and delivering a specially prepared infusate to the patient through the catheter.

In the case of infants, the catheter is ordinarily inserted in the operating room under the usual sterile techniques using local anesthesia. A transverse incision is made over the right sternocleidomastoid muscle, and after isolation of the external jugular vein, the catheter is intoduced and advanced to the desired point, its precise location being confirmed by x-ray study. The free end of the catheter is then placed under the skin at the incision and brought out some distance away behind the right ear in a subcutaneous location using a large bore hollow needle to facilitate the passage of the catheter beneath the skin. The incision is closed and antibiotic ointment and a dressing are applied to the exit point of the catheter after it has been secured in place with a silk suture with great care being taken to maintain the sterility of the exit site of the catheter. Conventional types of intravenous tubing are then attached to the free end of the catheter and the infusate is introduced into the patient using an infusion pump or the like.

In the case of infants, it is essential to have proper positioning of the catheter since improper positioning of the catheter can be responsible not only for complications but also for death in infants. Thus, X-ray control in the placing of the catheter in the operating room at the time of the initial placement is generally considered to be necessary.

It has been noted that infants (particularly newborns) engage in random, uncontrolled movement and great care must be taken to protect the catheter where it exits from the patient so that the catheter is not dislodged. Various techniques have been tried for anchoring the catheter at its exit site behind the ear, but such techniques have been inconvenient or inconsistent, or both.

BRIEF SUMMARY OF THE INVENTION

The present invention is an improved catheter. The improved catheters of the present invention consist essentially of a catheter tube to which is firmly attached a small transverse wing. This wing or cross bar is designed to be slipped into an incision below the skin and then held in place in the incised pocket when the skin around the incision is sewn together. This prevents inadvertent dislodgement and makes removal of the catheter a simple procedure.

However, because of the presence of the wing or cross bar, the technique for insertion of the catheter must be changed. In the new or modified technique, a first incision is made in the patient, usually behind the right ear. One of the ends of the catheter (called the "tail end") is then inserted under the skin of the patient through the incision using a large bore hollow needle to facilitate passage of the catheter tube beneath the skin. The tail end is then brought out through the skin of the patient, usually along the right side of the neck. The catheter tubing is then pulled from its exit point until the wing slips into the first incision and is positioned within the incision and below the skin. The skin around the incision is then sewn shut so as to embrace the wing in the subcutaneous pocket that has just been formed. If necessary, the tail of the catheter is then cut to a desired length and the tail is introduced into an appropriate vein. The opposite or inlet end of the catheter tube is then connected to a suitable source of infusate and alimentation is begun.

DETAILED DESCRIPTION

General Description

Figure 1:
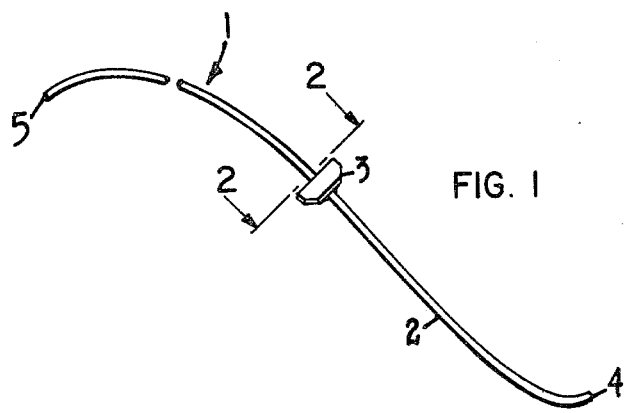
FIG. 1 is a perspective view of an improved catheter.

The following description is made with reference to the drawings in which FIG. 1 illustrates an improved catheter generally designated by the numeral 1. The catheter includes a thin catheter tubing (i.e. spaghetti like) 2 to which is firmly attached a cross bar or wing 3. One end 4 of the catheter tubing 2 has arbitrarily been called the "tail end" and the opposite end 5 has been called the "free end". The tail end is intended to be inserted into a vein and the free end is intended to be attached to a suitable source of infusate.

Figure 2:
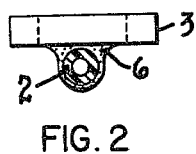
FIG. 2 is a cross-sectional view of the improved catheter of FIG. 1 taken along lines 2—2 of FIG. 1.

A cross-sectional view of the improved catheter is shown in FIG. 2. As shown in FIG. 2, the catheter tubing 2 is firmly bonded to wing 3 with an adhesive 6.

Figure 4:
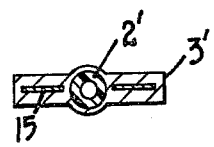
FIG. 4 is a cross-sectional view of an alternative catheter showing a different style wing.

As shown in the alternative embodiment of FIG. 4 the wing 3' may be reinforced (e.g. reinforced with a woven strip of synthetic fibers 15) and totally embrace catheter tube 2'.

Materials of Construction

The improved catheters of the present invention will be made of a biologically acceptable material which can be sterilized to avoid patient contamination.

Although the cross member 3 can be made of rigid materials, it is preferably made of a flexible, resilient material which can and often will be the same as or similar to the material used to make the tubing 2.

Although a variety of materials of construction can be used, synthetic rubbers, particularly silicone rubbers (e.g. SILASTIC ®, a silicone rubber manufactured by Dow Corning Corporation) are preferred. Silicone rubber is especially preferred because it is biologically acceptable, and similar adhesives (i.e. silicone rubber adhesives) exist which permit the convenient bonding of the small cross member 3 to the catheter tubing 2.

Regardless of the material chosen for the wing 3, it should be made so that its surface is substantially non-adherent to growing tissue. This is particularly true when dealing with infants. This is not a situation where it is advantageous to have the patients tissue "lock onto" the implantable device since the implant is intended to be temporary (e.g. 3 days to as much as two years).

Method of Use

Figure 3:
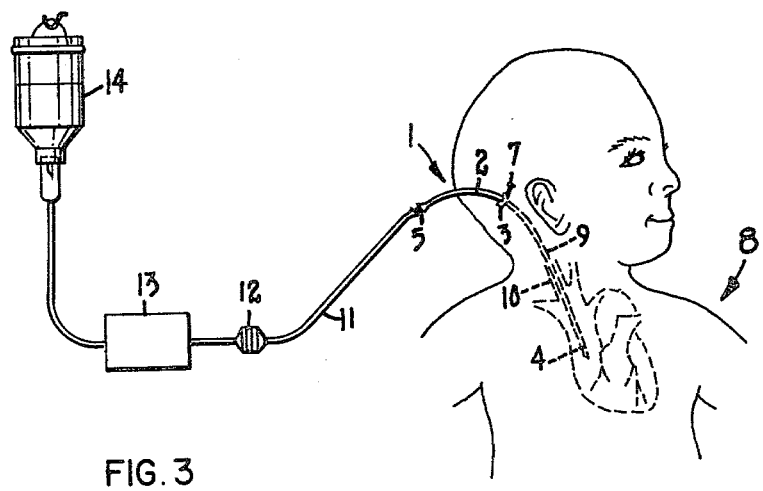
FIG. 3 is a diagram showing the delivery of the infusate through the improved catheter.

The method of use of the improved catheter 1 is shown in FIG. 3.

In the new or modified technique, a first incision 7 is made in the patient 8, usually behind the right ear. The tail end 4 of the catheter 1 is then inserted under the skin of the patient through the incision 7 using a large bore hollow needle (not shown) to facilitate passage of the catheter tube beneath the skin. The tail end 4 of the catheter 1 is then brought out through the skin of the patient 8 usually along the right side of the neck at exit point 9. The tail end 4 of catheter 1 is then pulled from exit point 9 until the wing 3 slips into the first incision and is positioned within the incision 7 and slides below the skin. The skin around the incision 7 is then sewn shut so as to embrace the wing 3 in the subcutaneous pocket that has just been formed. If necessary, the tail 4 of the catheter 1 is then cut to a desired length and the tail 4 is re-introduced at exit point 9 into an appropriate vein 10. The opposite or free end 5 of the catheter 1 is then connected to intravenous tubing 11, a micropore filter 12, an infusion pump 13 and a source of infusate 14. Alimentation is then begun.

What is claimed is:

1. The method of intravenous alimentation that comprises the steps of:
    (a) making a first incision in the patient;
    (b) inserting one end of a catheter tube having a small transverse wing made of a biologically acceptable material that is substantially non-adherent to growing tissue fixedly attached to said tube at a location along its length, through the first incision and routing the tubing under the skin through an exit point removed from the first incision;
    (c) withdrawing the tubing from the exit point until the transverse wing is under the skin at the edge of the first incision and surgically closing the first incision over the transverse wing;
    (d) cutting the portion of the tubing exiting from the exit point to a length appropriate so that, when it is reinserted through the exit point and under the skin, it is of an appropriate length for introduction into a suitable vein;
    (e) re-introducing the withdrawn tubing under the skin into a suitable vein; and
    (f) introducing a suitable infusate into the patient through said catheter.

2. A method in accordance with claim 1 further comprising a step of removing said catheter tube from the patient after completion of infusion treatment by withdrawing said tube through said first incision.

* * * * *